(12) United States Patent
Rosenblum et al.

(10) Patent No.: US 8,334,262 B2
(45) Date of Patent: Dec. 18, 2012

(54) COGNITIVE FUNCTION

(75) Inventors: Yaacov Rosenblum, Zichron Yaacov (IL); Elad Stern, Kibbutz Ma'ale Gilboa (IL); Yifat Segev, Haifa (IL)

(73) Assignee: Carmel-Haipa University Economic Corp. Ltd., Mount Carmel (IL)

( * ) Notice: Subject to any disclaimer, the term of this patent is extended or adjusted under 35 U.S.C. 154(b) by 0 days.

(21) Appl. No.: 12/827,935

(22) Filed: Jun. 30, 2010

(65) Prior Publication Data

US 2011/0052566 A1   Mar. 3, 2011

Related U.S. Application Data

(63) Continuation-in-part of application No. PCT/IB2009/007857, filed on Dec. 21, 2009.

(30) Foreign Application Priority Data

Dec. 23, 2008 (GB) .................................. 0823461.9
Dec. 23, 2008 (GB) .................................. 0823462.7

(51) Int. Cl.
*A01N 43/78* (2006.01)
*A61K 31/425* (2006.01)
*A61K 38/00* (2006.01)
*A61P 25/28* (2006.01)

(52) U.S. Cl. ....................... 514/17.8; 514/366

(58) Field of Classification Search .......................... None
See application file for complete search history.

(56) References Cited

U.S. PATENT DOCUMENTS

2003/0119017 A1   6/2003   McSwiggen

FOREIGN PATENT DOCUMENTS

| WO | 2006114019 A1 | 11/2006 |
| WO | 2009070378 A1 | 6/2009 |
| WO | 2010017541 A1 | 2/2010 |

OTHER PUBLICATIONS

Page et al. Activated double-stranded RNA-dependent protein kinase and neuronal death in models of Alzheimer's disease. Neuroscience, 139, 2006, 1343-1354.*
www.alz.org. What is Alzheimer's disease. 2011.*
Eley et al. Inhibition of activation of dsRNA-dependent protein kinase and tumour growth inhibition. Cancer Chemotherp. Pharmacol., 2009, 63: 651-659.*
Jammi et al. Small molecule inhibitors of the RNA-dependent protein kinase. Biochemical and Biophysical Research Communications, 308, 2003, 50-57.*
Page G et al; "Activated double-stranded RNA-dependent protein kinase and neuronal death in models of Alzheimer's disease" Neuroscience, vol. 139, No. 4, pp. 1343-1354, (2006).
Page G et al; "PKR is activated in Alzheimer's disease and in experimental models" Alzheimer's & Dementia: The Journal of the Alzheimer's Association, vol. 1, No. 1, p. 63, (2005).
Paccalin Marc et al; "Activated mTOR and PKR Kinases in Lymphocytes Correlate with Memory and Cognitive Decline in Alzheimer's Disease" Dementia and Geriatric Cognitive Disorders, vol. 22, No. 4, pp. 320-326, (2006).
Jammi N V et al; "Small molecule inhibitors of the RNA-dependent protein kinase" Biochemical and Biophysical Research Communications, vol. 308, No. 1, pp. 50-57, (2003).
Peel Alyson L; "PKR Activation in Neurodegenerative Disease" Journal of Neuropathology & Experimental Neurology, vol. 63, No. 2, pp. 97-105, (2004).
Chang Raymond C C et al; "Phosphorylation of eukaryotic initiation factor-2[alpha] (eIF2[alpha]) is associated with neuronal degeneration in Alzheimer's disease" Neuroreport, vol. 13, No. 18, pp. 2429-2432. (2002).
Mc Gowen et al.; "A decade of modeling Alzheimer's disease in transgenic mice" TRENDS in Genetics vol. 22 No. 5, pp. 281-289 (2006).
International Preliminary Examination Report on Patentability of PCT/IB2009/007857, issued Jun. 29, 2011.

* cited by examiner

*Primary Examiner* — Brandon Fetterolf
*Assistant Examiner* — Anna Pagonakis
(74) *Attorney, Agent, or Firm* — Browdy and Neimark, PLLC

(57) ABSTRACT

Inhibition of eIF-2α phosphorylation can be used to improve cognitive function and/or to treat dementia, including Alzheimer's Disease. In particular, this can be achieved by inhibiting the kinase activity of PKR in a non-toxic manner.

5 Claims, 9 Drawing Sheets

COGNITIVE FUNCTION

CROSS-REFERENCE TO RELATED APPLICATIONS

The present application is a Continuation-in-Part of International Application No. PCT/IB2009/007857, filed Dec. 21, 2009, in which the United States is designated, and claims the benefit of priority from United Kingdom Applications No. 0823461.9, filed on Dec. 23, 2008 and No. 0823462.7, filed on Dec. 23, 2008 the entire contents of each and all these applications being hereby incorporated by reference herein in their entirety as if fully disclosed herein.

FIELD OF THE INVENTION

The present invention relates to improving cognitive function, and in particular, to improving learning and/or memory formation. The present invention also relates to treating dementia and in particular to treating Alzheimer's Disease (AD).

BACKGROUND OF THE INVENTION

Enhancing cognitive function in humans is a major target for drugs companies and the health industry. However, so far there has been very little success. Current techniques can be categorised as follows: a) fighting biochemical deterioration with age or disease; and b) identifying neurotransmitter systems or signal transduction that can enhance neuronal function.

AD is one of the most common forms of dementia. It is generally diagnosed in people over the age of 65 years, although early onset is possible. AD is a progressive and terminal disease, for which there is currently no cure.

The ability to form new and stable memories deteriorates with age and is a clear hallmark of different neurodegenerative diseases including AD and frontotemporal dementia. The vast majority of AD cases have complex etiology with multiple genetic and environmental factors influencing pathogenesis. Indeed, different animal models are used to study the complex biology underlying AD (Gotz & Ittner (2008) *Nature Reviews Neuroscience* 9, 532-544).

Control of mRNA translation is a major means for regulation of gene expression in responses to external stimuli presented by the changing environment. Translation regulation comprises three major steps: initiation, elongation and termination, where, in eukaryotes, the initiation phase is usually rate-limiting and serves as the target for regulation. Several major signal transduction cascades, including the mTOR and eIF2α pathways, regulate translation initiation in neurons and other cells. Translation regulation in neurons is particularly complex. Major components of the protein synthesis machinery, including ribosomes, translation factors and mRNA are present in dendrites and dendritic spines, and translation can be regulated differentially at the cell body, the synapse and post-synaptic components. Importantly, cellular stress and injury often lead to an increase in phosphorylation of initiation-related proteins such as eIF2α and to subsequent down-regulation of the translation initiation process. The effects of neuronal activity and of distinct neurotransmitter systems on these signalling cascades, and their role in learning and memory and neuronal plasticity are not fully understood.

Initiation factor eIF-2 is a protein synthesis initiation factor, the activity of which is reduced in a controlled way by phosphorylation of its alpha subunit (eIF-2α). It has previously been shown (Costa-Mattioli et al. (2007) *Cell* 129, 195-206) that heterozygous mice in which the phosphorylation site of eIF-2α was mutated (and thus phosphorylation of eIF-2α was reduced) had improved cognitive function.

Other recent publications of interest include: Belelovsky et al. (2005) *European Journal of Neuroscience* 22, 2560-2568; Banko et al. (2006) *Neurobiology of learning and memory* 87, 248-256; Antion et al. (2008) *Learning and memory* 15, 29-38; Costa-Mattioli et al. (2005) *Nature* 436, 1166-1173; Paccalin et al. (2006) *Dementia and Geriatric Cognitive Disorders* 23, 320-326; Chang et al. (2002) *Neuroreport* 13, 2429-2432; Page et al. (2006) *Neuroscience* 139; 1343-1354; Kim et al. (2007) *Journal of Neuroscience Research* 85; 1528-1537; Bullido et al. (2008) *Neurobiology of Aging* 29, 1160-1166; Davis et al. (1984) *Psychological Bulletin* 96, 518-559; Nguyen et al. (1994) *Science* 265, 1104-1107; and Schicknick et al. (2008) *Cerebral Cortex* 18, 2646-2658.

The above disclosures teach the genetic modification of animals to improve cognitive function. However, there are many difficulties and much expense associated with such techniques. These solutions are therefore not currently practical.

SUMMARY OF THE INVENTION

According to a first aspect of the present invention, there is provided an inhibitor of eIF-2α, for use in improving cognitive function.

In an embodiment, the inhibitor is an inhibitor of a kinase, and may inhibit the kinase activity of PKR. The inhibitor may act to inhibit the ATP-binding site of a kinase, such as PKR.

Preferably, the inhibitor is for use in improving learning and/or for use in improving memory formation. The inhibitor may be for use in treating dementia, in particular, Alzheimer's Disease.

Preferably, the inhibitor is not for administration directly to the brain. In particular, the inhibitor may be for oral administration or injection.

In a preferred embodiment, the inhibitor is able transiently to inhibit eIF-2α.

The inhibitor is preferably a small molecule. For example, the inhibitor may be an oxindole/imidazole derivative, such as Compound 16.

In other embodiments, the inhibitor may be a protein, such as a peptide or an antibody.

In further embodiments, the inhibitor may be a nucleic acid. For example, the inhibitor may be an RNA, such as antisense RNA or a double stranded RNA.

According to a second aspect of the present invention, there is provided use of an inhibitor as described above in the manufacture of a medicament for improving cognitive function.

The use may, in particular, be for improving learning and/or for improving memory formation.

According to a third aspect of the present invention, there is provided a method of improving cognitive function, including inhibiting an eIF-2α kinase by administering to a patient an inhibitor as described above.

According to a fourth aspect of the present invention, there is provided a method of improving cognitive function including inhibiting the kinase activity of PKR.

According to a fifth aspect of the present invention, there is provided an inhibitor of eIF-2α, for use in treating dementia.

In an embodiment, the inhibitor is an inhibitor of a kinase, and may inhibit the kinase activity of PKR. The inhibitor may act to inhibit the ATP-binding site of a kinase, such as PKR.

Preferably, the inhibitor is for use in treating AD, and may be for use in improving cognitive function in a patient with dementia or AD.

Preferably, the inhibitor is not for administration directly to the brain. In particular, the inhibitor may be for oral administration or for injection.

In a preferred embodiment, the inhibitor is able transiently to inhibit eIF-2α.

The inhibitor is preferably a small molecule. For example, the inhibitor may be an oxindole/imidazole derivative, such as Compound 16.

In other embodiments, the inhibitor may be a protein, such as a peptide or an antibody.

In further embodiments, the inhibitor may be a nucleic acid. For example, the inhibitor may be an RNA, such as antisense RNA or a double stranded RNA.

According to a sixth aspect of the present invention, there is provided use of an inhibitor as described above in the manufacture of a medicament for treating dementia.

The use may, in particular, be for treating AD and/or for improving cognitive function in a patient with dementia.

According to a seventh aspect of the present invention, there is provided a method of treating dementia, including inhibiting an eIF-2α kinase by administering to a patient an inhibitor as described above.

According to a eighth aspect of the present invention, there is provided a method of treating dementia including inhibiting the kinase activity of PKR.

BRIEF DESCRIPTION OF THE DRAWINGS

Embodiments of the present invention are described below, by way of example only, with reference to the accompanying drawings, in which.

DETAILED DESCRIPTION OF THE INVENTION

Figure 1:
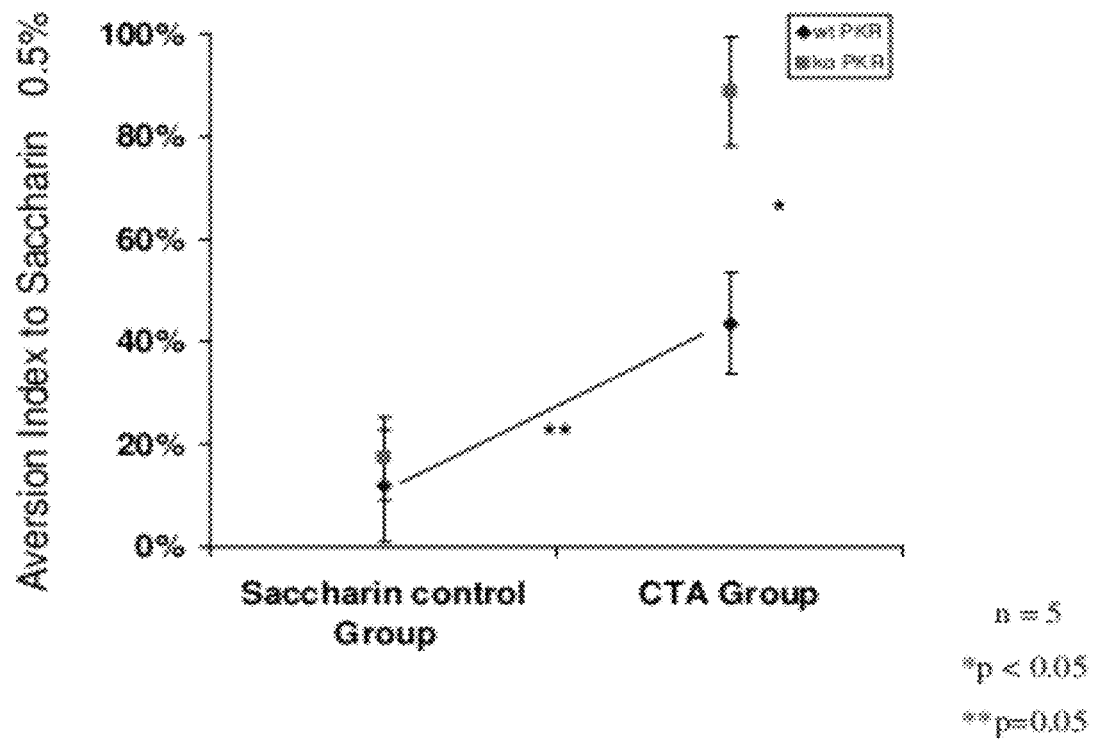
FIG. 1 shows enhanced conditioned taste aversion (CTA) in PKR knockout mice.

A crucial post translation event that controls translation initiation is the phosphorylation levels of Ser-51 eIF-2α. Phosphorylation level is known to be controlled by four different kinases and one specific phosphatase, and can be modulated via different extra- and intra-cellular inputs. However, the specific contribution of these kinases and the upstream signal transduction in the normal and in the neurodegenerate brain are not known. Levels of eIF-2α phosphorylation in genetically engineered mice have been shown to be inversely correlated with memory and synaptic plasticity consolidation (Costa Mattioli et al., (2007)). The crucial role that eIF-2α phosphorylation plays in consolidation processes was studied using genetic manipulations (i.e. knockouts of GCN2 or replacement of Ser-51 with an alanine residue to disrupt the phosphorylation site of eIF-2α).

One of the four eIF-2α phosphorylation kinases is known as protein kinase R (PKR). PKR is an RNA-dependent, interferon-induced serine/threoine protein kinase. PKR regulates phosphorylation of Ser-51 of eIF-2α. The present applicant has investigated the role of PKR in phosphorylation of eIF-2α, and the subsequent effects on cognitive function. The applicant has found that, surprisingly, PKR is highly expressed within brain neurons and its phosphorylated (active) form within synapses. The active form of PKR has thus been shown by the applicant to be present in the right place for control of synaptic processes underlying memory consolidation. The applicant therefore considered whether disrupting the function of PKR (and thus disrupting phosphorylation of eIF-2α thereby enhancing local or general neuronal translation) could provide improved cognitive function in animal models.

In one aspect, the present invention provides a method for improving cognitive function, said method comprising administering to a patient in need a therapeutically effective amount of an inhibitor of eIF-2α phosphorylation or a pharmaceutically acceptable salt thereof such as to improve cognitive function in said patient.

In certain embodiments, the present invention provides a method for improving cognitive function, said method comprising administering to a patient in need a therapeutically effective amount of an inhibitor of the kinase activity of PKR or a pharmaceutically acceptable salt of said inhibitor such as to improve cognitive function in said patient.

In one aspect, the present invention provides a method for treating dementia, said method comprising administering to a patient in need a therapeutically effective amount of an inhibitor of an eIF-2α kinase or a pharmaceutically acceptable salt of said inhibitor such as to inhibit said eIF-2α phosphorylation and improve cognitive function in said patient.

In certain embodiments, the present invention provides a method for treating dementia, said method comprising administering to a patient in need a therapeutically effective amount of an inhibitor of the kinase activity of PKR or a pharmaceutically acceptable salt of said inhibitor such as to improve cognitive function in said patient.

In certain embodiments, the patient with dementia suffers from Alzheimer's disease and the method of the invention is used for treating Alzheimer's disease.

As used herein, the term "cognitive function" is used to define any mental process that involves symbolic operations such as perception, memory, creation of imagery, thinking, awareness and capacity for judgment. An improvement of one or more of these functions in a patient will signify an improvement of the cognitive function in said patient. Several tests are known to the skill in the art to measure improvement in any of these processes.

An inhibitor of eIF-2α phosphorylation, in particular an inhibitor of the kinase activity of PKR, or any pharmaceutically acceptable salt thereof is used according to the invention. In certain preferred embodiments, the PKR inhibitor is the oxindole/imidazole derivative of Formula I herein or a pharmaceutically acceptable salt thereof. Other known PKR inhibitors or PKR inhibitors screened by the method as described in the above-mentioned Jammi et al., 2003, can be tested for their suitability to improve cognitive function and used according to the invention.

According to the present invention, the inhibitors can be in the form of pharmaceutically acceptable salts. Pharmaceutically acceptable salts can be prepared by treatment with inorganic bases, for example, sodium hydroxide or inorganic/organic acids such as hydrochloric acid, acetic acid, citric acid and the like.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound used in the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It is to be understood that, as used herein, references to the small molecule inhibitor are meant to also include the pharmaceutically acceptable salts thereof.

The present invention also provides pharmaceutical compositions comprising an inhibitor of eIF-2α phosphorylation, in particular an inhibitor of the kinase activity of PKR or any pharmaceutically acceptable salt thereof as the active ingredient and a pharmaceutically acceptable carrier.

The pharmaceutical compositions of the present invention can be formulated for administration by a variety of routes including oral, rectal, transdermal, subcutaneous, intravenous, intramuscular, and intranasal. Such compositions are prepared in a manner well known in the pharmaceutical art and comprise the active ingredient along with an excipient or a carrier. During the preparation, the active ingredient is usually mixed with an excipient or carrier or diluted by an excipient. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols, soft and hard gelatin capsules, suppositories, sterile injectable solutions, and sterile packaged powders.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methylcellulose. The formulations can additionally include lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art.

The compositions are preferably formulated in a unit dosage form, each dosage containing from about 0.1 to about 500 mg. The term "unit dosage forms" refers to physically discrete units suitable as unitary dosages for human subjects and other mammals, each unit containing a predetermined quantity of the active compound calculated to produce the desired therapeutic effect, in association with a suitable pharmaceutical excipient.

The active ingredient is effective over a wide dosage range and is generally administered in a therapeutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings; such materials include a number of polymeric acids and mixtures of polymeric acids with materials such as shellac, cetyl alcohol, and cellulose acetate.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 incorporated herein by reference as if fully set forth. Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions, which can transiently open the blood-brain barrier.

As used herein, the term "treatment" or "treating" is intended to include the administration of the inhibitor as defined herein for improving cognitive function of a patient in need, e.g., a patient suffering from dementia, particularly a patient suffering from Alzheimer's disease. Further, such treatment may be used in conjunction with other treatments for improving cognitive function known to those of skill in the art.

The invention will now be illustrated by the following Examples, which are non-limitative.

Example 1

The applicant analysed taste learning in PKR knockout mice. The mice were homozygous for a mutation in the gene encoding PKR, and thus lacked any expression of PKR. Two groups of mice were tested for CTA learning for 0.5% saccharin as described below. Both groups exhibited similar behaviour up to the test days.

It was found that both wild-type and PKR knockout mice show CTA learning (the aversion is increased compared to non-conditioned mice). However, the PKR knockout mice show much better memory for CTA training (40% versus 90%).

The results are illustrated in FIG. 1, which shows that CTA is enhanced in PKR knockout mice.

Furthermore, the PKR knockout mice showed no deleterious side effects. The sole observed side effect was the improvement in the CTA test compared to the control group.

The results obtained in Example 1 demonstrate that animals that are unable to express PKR have improved cognitive function. Without PKR, there is a reduction in phosphorylation of eIF-2α. The results demonstrate that disrupting PKR is a viable means to obtain improved cognitive function.

Having demonstrated the principle of improving cognitive function by disrupting PKR function, the applicant sought to identify PKR inhibitors able transiently to disrupt PKR activity. However, a major issue with the use of such inhibitors is whether or not they are able to reach the site in the body where their activity is required. In particular, for such an inhibitor to be administered orally it must be able to cross the blood-brain barrier, which can be problematic for many drugs.

Compound 16 (C-16) is an oxindole/imidazole derivative that is able to inhibit PKR's kinase activity by inhibiting the ATP-binding site of PKR (Jammi et al. (2003) *Biochemical and Biophysical Research Communications* 308, 50-57). Compound 16 is available commercially, for example, from Calbiochem® and has the structure shown by

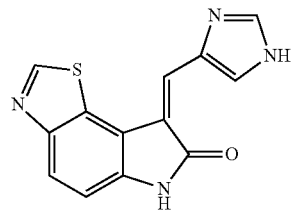

compound 16

The applicant has used C-16 to investigate the effect of inhibiting the kinase activity of PKR on phosphorylation of eIF-2α in vivo and also on the cognitive function of rats treated with C-16. The results of these investigations are presented in Examples 2 to 6 below.

Example 2

In order to test biochemically the ability of C-16 to reduce eIF-2α phosphorylation in the mature brain, C-16 was applied to hippocampal slices from mature rats substantially as described by Kaphzan et al. (2007) *Journal of Neurochemistry* 103, 388-399 but with modifications as set out below.

After decapitation the brain was immediately immersed in cold (4° C.) carboxygenated (95% $O_2$, 5% $CO_2$) Artificial Cerebro-Spinal Fluid (ACSF [in mM]: 124 NaCl, 5 KCl, 1.2 $MgSO_4$, 1.2 $NaH_2PO_4$, 26 $NaHCO_3$, 10 D-glucose, 2.4 CaCl), and after about 120s both hippocampi were dissected out in a plate filled with cold (4° C.) ACSF on ice. The hippocampi were put on a cooled stand of a McIlwain tissue chopper TC752 (Campden Instruments Ltd, UK), cut into 400-µm slices, and then put back into a chamber filled with carboxygenated cold (4° C.) ACSF.

The slices were transferred to a holding chamber for about 20-30 min, to reach room temperature, and were then transferred to a six-chamber pharmacological instrument, designed to our specifications by Scientific Systems Design Company (Ontario, Canada). All of the slices tested in any one experiment (i.e., in all six chambers) were produced by the same procedure from the same rat. The hippocampal slices were heated to 32° C. and were kept in the chamber for 5 h before any pharmacological intervention. Each chamber contained four slices. The slices were perfused with heated and carboxygenated ACSF (with or without 50 µM C-16 (experimental and control groups respectively)) via a Model MP3 peristaltic pump (Gilson, France), at a rate of ~2 mL min for 10 mins. The chamber space was carboxygenated and humidified. The chamber was an interface type, and the slices were placed upon a lens paper.

The slices were analysed occasionally for their viability using extracellular recordings of fEPSP in the CA1 region. 10 min following insulin application (1.5 µM)/control condition, the slices were removed from the pharmacological chamber and snap frozen on dry ice. After freezing, slices were homogenized in SDS sample buffer as previously described (Rosenblum et al., (1997) *Journal of Neuroscience* 17, 5129-5135). Four slices from each chamber were combined as two pairs and the two slices of each pair were homogenised as a single sample, so that each chamber yielded two samples.

Figure 2:
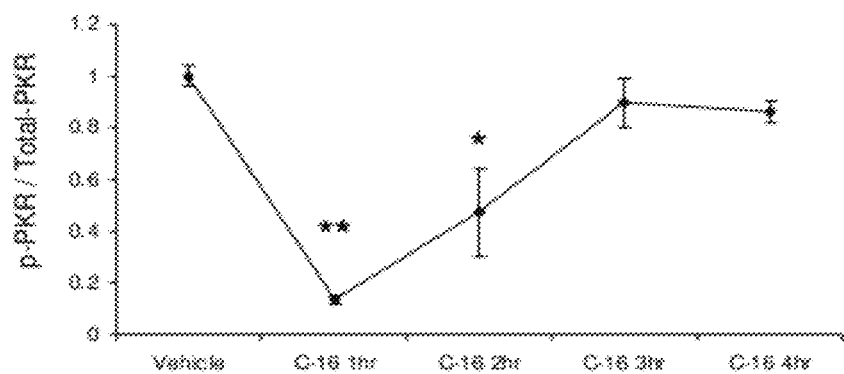
FIG. 2 shows decrease in phosphorylation of PKR.
Figure 3:
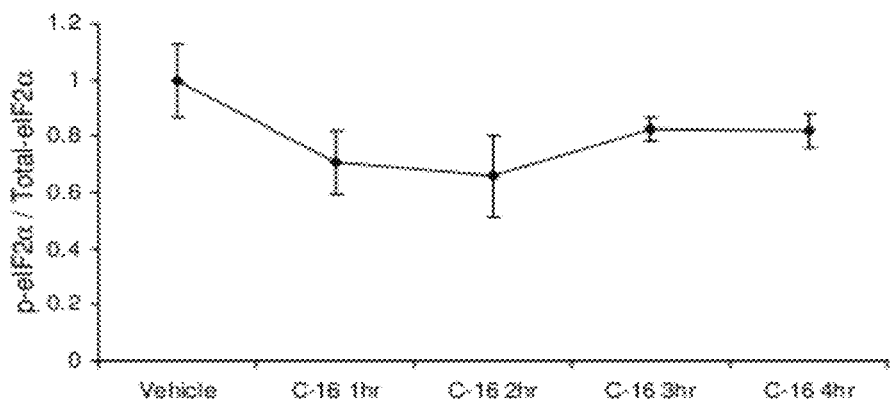
FIG. 3 shows decrease in phosphorylation of eIF-2α.

The results are illustrated in FIGS. 2 and 3, which show that C-16 inhibited both PKR (FIG. 2) and eIF-2α (FIG. 3) phosphorylation in the mature hippocampus. The time window of C-16 effect was analysed by Western blot using specific antibodies for phosphorylated and dephosphorylated forms of PKR and eIF-2α. A strong effect after 1 hr, returning to base line 3-4 hr following treatment, was identified. (*p<0.05 or **p<0.01 (Vehicle: n=4, C-16: n=2 for each time point). All results are means±S.E.M.)

These results demonstrate the potent ability of C-16 to block transiently PKR phosphorylation and eIF-2α phosphorylation in the mature brain.

Example 3

The phosphorylation levels of eIF-2α in the gustatory cortex were measured following novel taste learning. It is highly accepted today that long term memories are stored in the cortex. Taste learning and CTA are major models for analysing implicit learning processes. It has previously been shown that electrophysiological and biochemical modifications in the gustatory cortex are both correlated and necessary for the formation and maintenance of taste memories (Rosenblum et al. (1997); Merhav & Rosenblum (2008) *Learning and Memory* 15, 501-507).

CTA was performed as described earlier (Rosenblum et al., (1993) *Behavioral and Neural Biology* 59, 49-56). Saccharin (0.1% w/v, sodium salt) or NaCl (0.3%) were used as the unfamiliar taste in training (i.e. the conditioned stimulus (CS)), and injection of LiCl (0.15 m, 2% body weight, i.p.) as the malaise-inducing agent (unconditioned stimulus (UCS)). At the beginning of the behavioral experiment, the rats were trained for 3 days to obtain their daily water ration once a day for 15 min from two pipettes each containing 10 mL of water. On the conditioning day, they were allowed to drink the saccharin solution instead of water from similar pipettes for 15 min, and 50 min later were injected with LiCl. Under these conditions, 2 days after training the conditioned rats preferred water to saccharin in a multiple choice test situation (three pipettes with 5 mL of saccharin each and three with 5 mL of water each), whereas non-conditioned rats preferred saccharin to water. The behavioural data are presented in terms of aversion index, defined as [mL water/(mL water+mL saccharin)] consumed in the test; 0.5 is a chance level, and the higher the aversion index, the more the rats prefer water to the conditioned taste.

In some experiments, a latent inhibition (LI) procedure (Rosenblum et al., (1993)) was combined with CTA to further isolate the effect of taste learning from the potential confounding effects of the UCS and the CS-UCS association. Latent inhibition is a process by which pre-exposure to a sensory stimulus diminishes the ability of that same stimulus to serve as an associated stimulus in subsequent learning. Thus, exposure of rats to an unfamiliar taste several days before this same taste serves as the CS in CTA training and significantly reduces the acquired aversion (Rosenblum et al. (1993)). Under such conditions, the degree of aversion after CTA training is a measure of the memory for saccharin acquired incidentally in the pre-CTA trial. In LI experiments, the rats were exposed to saccharin for 15 min, in either three, two or one pipette of 5 mL or two 10 mL pippetes of saccharin, 2 days before CTA training, as described above, in which saccharin was used as the CS. Testing was also as described above for the usual CTA procedure. Briefly, two groups of rats were water-deprived for 24 hours, then pre-trained for 3 days to obtain their daily water ration once a day for 15 mins from two pipettes each containing 10 mL of water. On the fourth day, the experimental group was exposed for 15 mins to unfamiliar taste (saccharin 0.1% or NaCl 0.3%), whilst the control group was exposed for the same time period to water (Rosenblum et al., (1993)).

Figure 4:
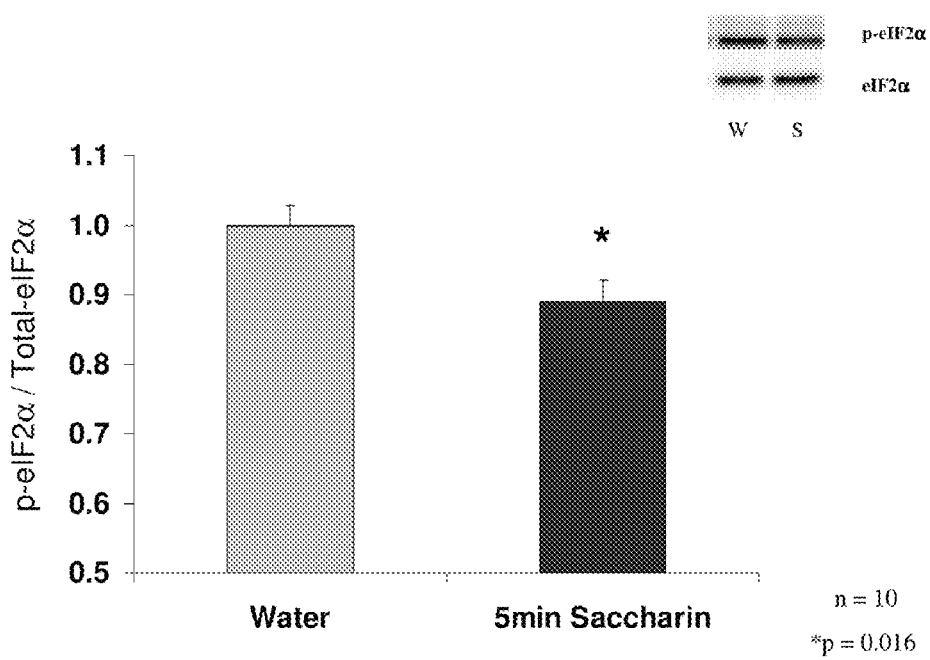
FIGS. 4 to 6 show dephosphorylation of eIF-2α.
Figure 5:
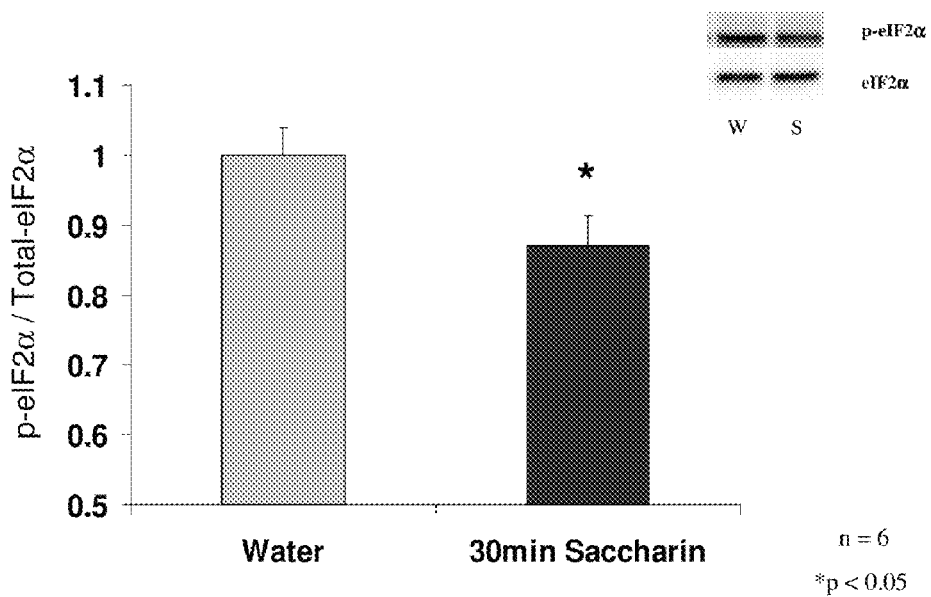
Figure 6:
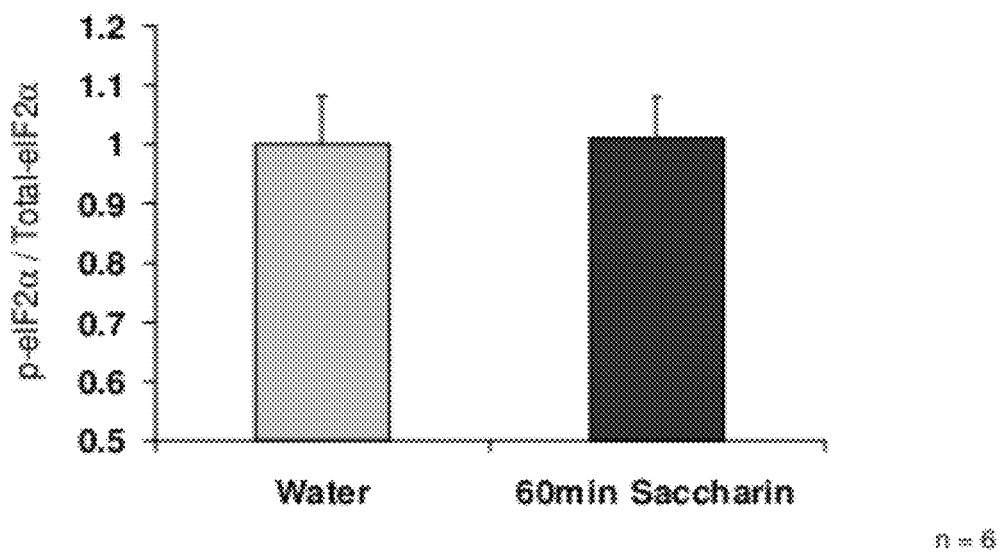

FIGS. 4 to 6 show that dephosphorylation of eIF-2α occurs in the gustatory cortex at 5 and 30 min, but not 60 min, following novel taste learning. It has therefore been shown that dephosphorylation of eIF-2α correlates with novel taste learning and that phosphorylation levels of eIF2α– will be negatively correlated with cortical-dependent learning.

Example 4

Figure 7:
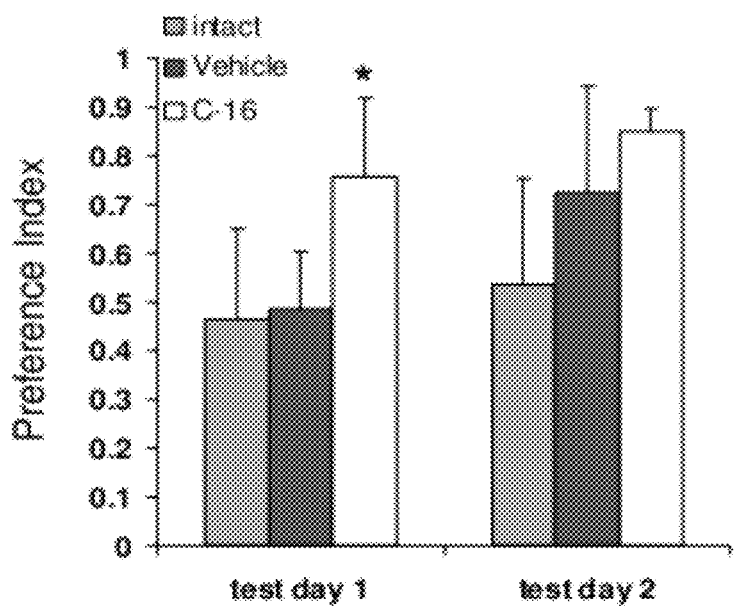
FIGS. 7 and 8 show enhanced novel taste memory.

The results above indicate that C-16 can be used as a cognitive enhancer. The ability of C-16 to enhance memory directly was then tested, first using local microinjection of C-16 to the gustatory cortex (FIGS. 8 and 10) and later via intraperitoneal (i.p.) injection (FIGS. 7 and 9).

In the local injection experiment, rats were cannulated with guiding cannula to the gustatory portion of the insular cortex as described before (Rosenblum et al., (1993)). Micro-infusions into the insular cortex were performed via chronically implanted cannulae. Rats were anesthetised with Equithesin (0.45 ml/100 g) (2.12% w/v $MgSO_4$, 10% v/v ethanol, 39.1% v/v 1,2, -propranolol, 0.98% w/v sodium pentobarbital, and 4.2% w/v chloral hydrate), restrained in a stereotactic apparatus (Stoelting, USA) and implanted bilaterally with a 10 mm guide stainless cannula (23 gauge) aimed at the rat gustatory cortex (anteroposterior, +1.2 mm relative to bregma; lateral, ±5.5 mm; ventral, –5.5 mm) The cannulae were positioned in place with acrylic dental cement and secured by two skull screws. A stylus was placed in the guide cannula to prevent clogging. Following the microsurgery, animals were injected intramuscularly (i.m.) with antibiotic and were allowed to recuperate for one week.

For micro-infusion, the stylus was removed from the guide cannula, and a 28 gauge injection cannula, extending 1.0 mm from the tip of the guide cannula, was inserted. The injection cannula was connected via PE20 tubing to a Hamilton microsyringe driven by a microinfusion pump (CMA/100; Carnegie Medicin). Microinfusion was performed bilaterally in a 1.0 μL volume per hemisphere delivered over 1 min. The injection cannula was left in position before withdrawal for an additional 1 min to minimise dragging of the injected liquid along the injection tract.

For the behavioural set of experiments, the rats were injected bilaterally either with C-16 (50 μM 0.5% DMSO in saline) or with vehicle (0.5% DMSO in saline), 120 min before the preexposure in the LI paradigm or the taste consumption in the CTA paradigm.

In both methods (i.e. LI and CTA training), there was a clear enhanced memory for both positive (LI paradigm) and negative (CTA paradigm) learning tasks demonstrating that C-16 by itself acts on cognition and not reinforcement.

FIG. 7 shows that C-16 enhances novel taste memory of 0.1% Saccharin 2 hr after i.p. application. (t-test: *p<0.01, n=6).

Figure 8:
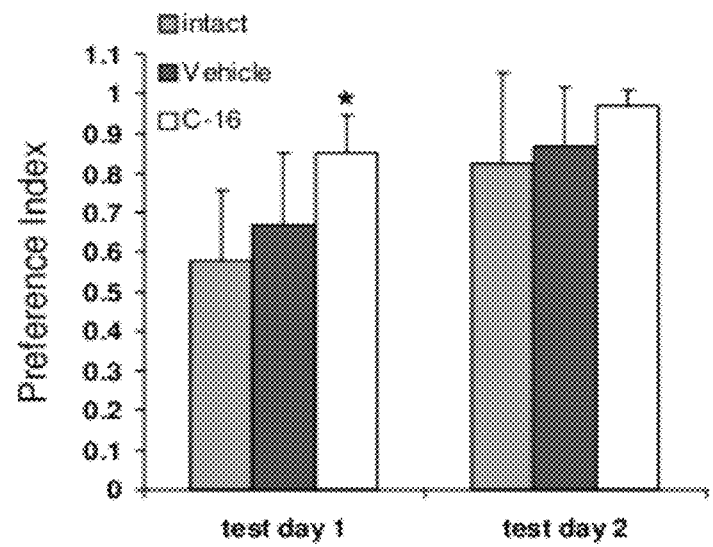
Figure 9:
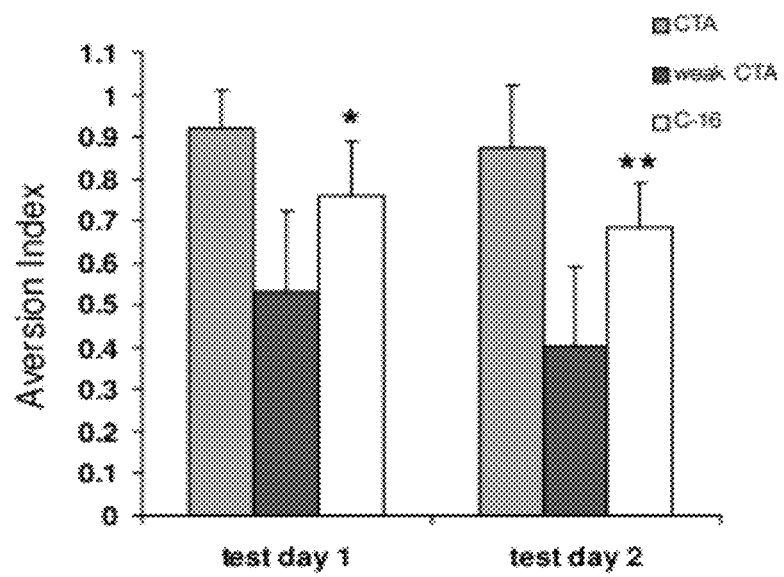
FIGS. 9 and 10 show enhanced CTA.

FIG. 8 shows that C-16 enhances novel taste memory of 0.1% Saccharin 30 min after local microinjection into the gustatory cortex. *p<0.05 (Vehicle: n=8, C-16: n=7).

FIG. 9 shows that C-16 enhances weak Conditioned Taste Aversion (0.05M) to 0.3% NaCl 2 hr after i.p. application. (t-test: *p<0.05 or **p<0.01, n=8).

Figure 10:
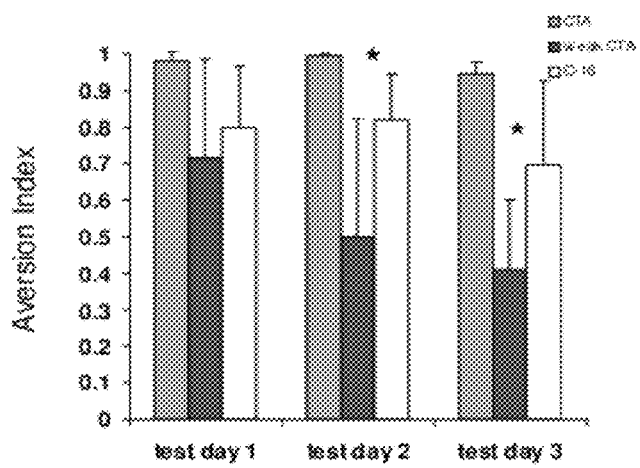

FIG. 10 shows that C-16 enhances weak CTA (0.05M) to 0.3% NaCl 30 min after local injection into the gustatory cortex. *p<0.05 (Weak CTA: n=7, C-16: n=6).

All results are means±S.E.M.

These results show that both local and i.p. injection of C-16 enhanced cortical dependent cognitive function and long term safe and unsafe taste memory. Conditioned taste aversion and novel taste learning were enhanced. Moreover, it has been shown that C-16 causes no other effect that could be measured and the effect was strong and significant.

Surprisingly it is not necessary to administer C-16 directly into the brain. This lends support to the possibility of oral administration of an inhibitor of eIF-2α phosphorylation to improve cognitive function.

Example 5

A test of odour role learning was carried out.

Subjects and apparatus: Age-matched young adult Sprague-Dawly male rats were used. Prior to training they were maintained on a 23.5 hr water-deprivation schedule, with food available ad libitum. Olfactory discrimination training protocol was performed daily on each trained and pseudo-trained rat in a 4-arm radial maze, as previously described (Cohen-Matsliah et al. (2007) *Journal of Neuroscience* 27, 12584-12589), with commercial odours that are regularly used in the cosmetics and food industry.

C-16 was injected i.p. every day, 2 hr before odour maze training. There was 48 hr break between day 3 and 4 without training or injection.

Training: Olfactory training consisted of 20 trials per day for each rat as previously described (Cohen-Matsliah et al. (2007)). In short, in each trial the rat had to choose between two odours (positive- and negative-cue) presented simultaneously. Rats designated to the trained group were rewarded upon choosing the positive cue. The criterion for learning was at least 80% positive-cue choices in the last 10 trials of a training day, as was previously used (Cohen-Matsliah et al. (2007)). Training for a new pair began only after training for the second pair was completed for all rats.

Figure 11:
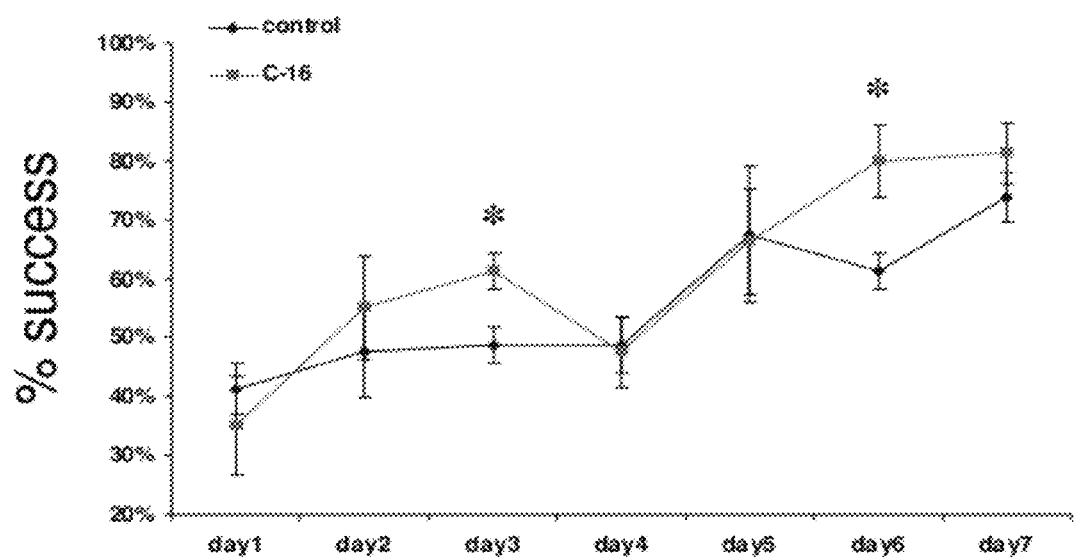
FIG. 11 shows enhanced odour maze learning.

The results obtained are presented in FIG. 11, which shows that C-16 enhances odour maze learning. In day 3 & 6 *p<0.05 (n=4). All results are means±S.E.M.

It is to be noted that in this experiment, C-16 was injected i.p. multiple times (once a day over a period of more than 7 days) without any clear disadvantageous side effect.

Example 6

A test of fear learning was carried out.

The entire behavioural procedure took place in the same conditioning chamber containing floor grids and transparent Plexiglas walls. The context of the chamber served as a conditioned stimulus (CS). Rats were placed in the chamber for an approximately two minute adjustment before they were given a foot-shock (0.8 mA for 0.5 sec), which was delivered to the floor bars and served as the unconditioned stimulus (US). The CS-US pairings were given three times. The inter-trial interval was 90-120 seconds throughout. The video images are transferred to a computer (fear-conditioning experiments, control experiment, Dell OptiPlex GXpro) equipped with an analysis program (Image (http://rsb.info.nih.gov/nih-image)) and a macroprogram (P. Schmid, Behavioral Neurobiology Laboratory, Swiss Federal Institute of Technology Zurich). The percentage of changed pixels between two adjacent 1 s images from one of the test boxes was used as a measure of activity. Freezing is commonly identified as cessation of any movement except for respiratory movements. If the percentage of changed pixels between two adjacent 1 s images was <0.05%, this corresponded well to such immobility and the behavior of the rat was scored as "freezing" for the respective second.

Figure 12:
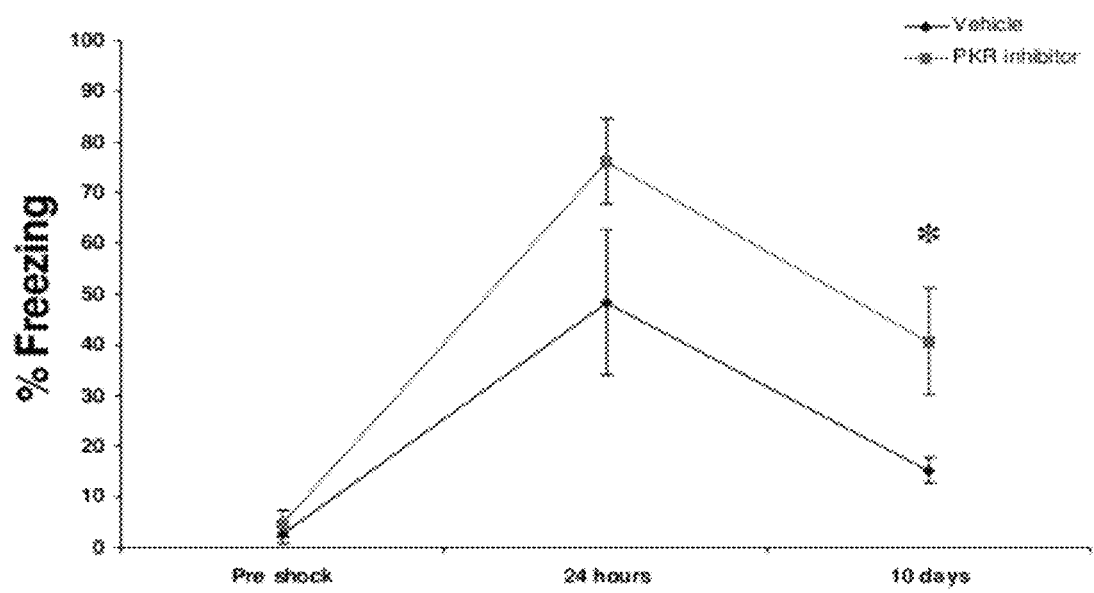
FIG. 12 shows enhanced contextual fear condition.

The results are presented in FIG. 12, which shows that C-16 enhances contextual fear condition. C-16 was injected i.p. 2 hr before contextual fear condition. Twenty-four hours and 10 days later the rats were tested in the same context without shock for 9 minutes. The results show the average freezing between the 4$^{th}$ and the 7$^{th}$ minutes. *p<0.05 (Vehicle: n=6, C-16: n=5). Repeated measure: F=9.1762; p=0.0143. All results are means±S.E.M.

Example 7

Figure 13:
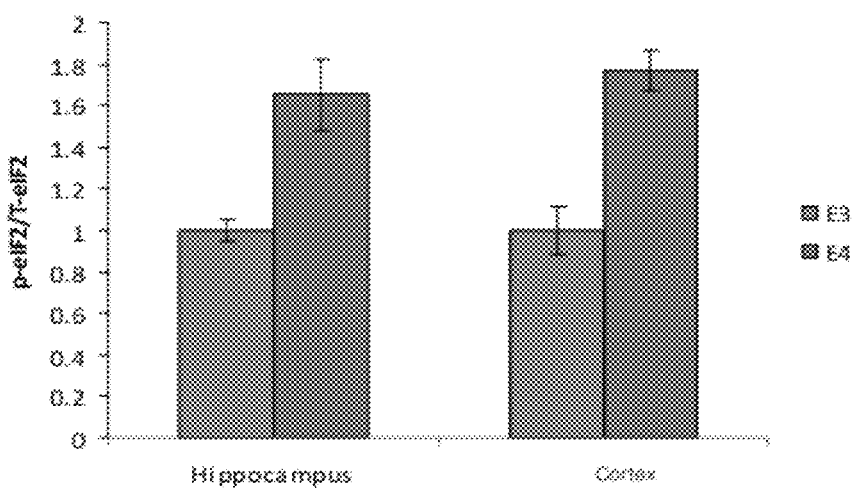
FIGS. 13 and 14 show the effects of apoE4 on phosphorylation of eIF2α in young mice.

ApoE4 is a prevalent genetic risk factor of AD. Hippocampus and cortex of young (3-4 months) apoE3 or apoE4 mice were homogenised and immunoblotted with antibodies that specifically recognise eIF2α and phosphorylated eIF2α (Ser 51). The results presented in FIG. 13 (n=4 per group) are the ratio of the intensities of the phosphorylated eIF2α to total eIF2α immunoblot bands, which is a measure of the extent of phosphorylation of this protein. As can be seen the extent of phosphorylation of this protein in the apoE4 mice is higher than in the corresponding apoE3 mice (*p<0.05, **p<0.01).

Figure 14:
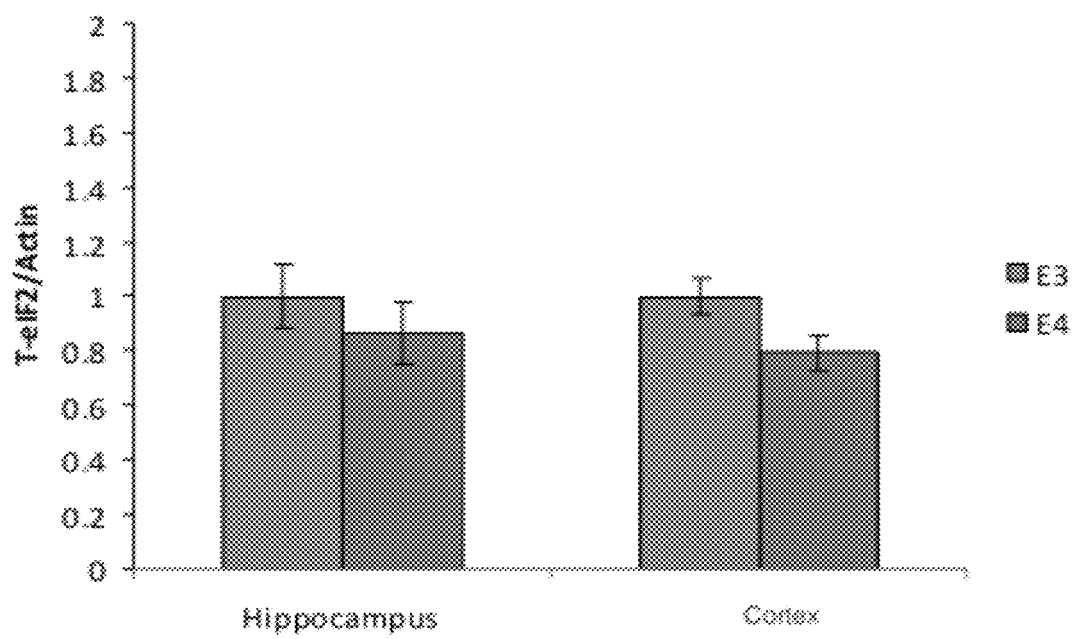

FIG. 14 demonstrates no modulation in the total amount of eIF2α protein (T-eIF2α) when compared with actin levels. This difference suggests that a translation initiation is attenuated isoform-specifically in the apoE4 young mice both in the cortex and hippocampus.

Example 8

Figure 15:
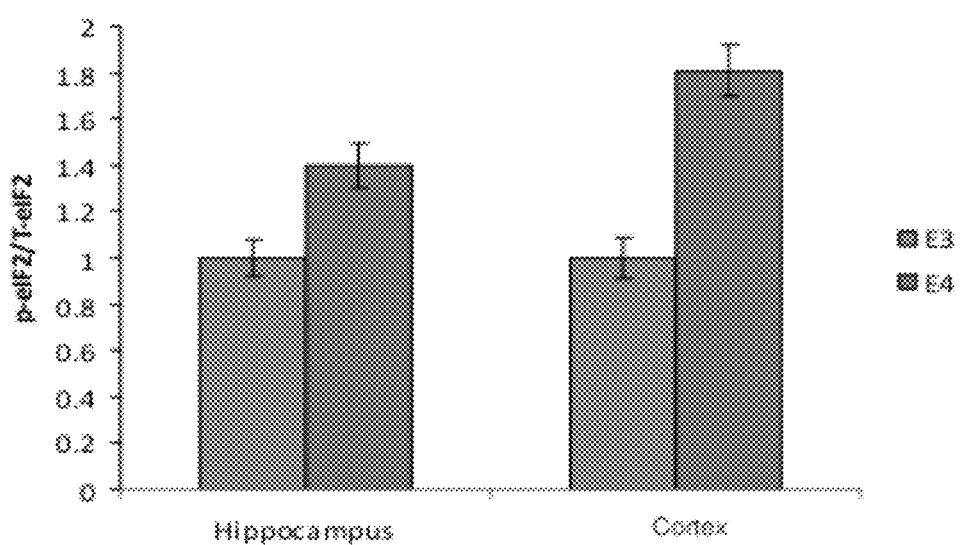
FIGS. 15 and 16 show the effects of apoE4 on phosphorylation of eIF2α in old mice.

Hippocampus and cortex of old (18 months) apoE3- or apoE4-expressing mice were homogenised and immunoblotted with antibodies that specifically recognise eIF2α or phosphorylated eIF2α (Ser 51). The results presented in FIG. 15 (n=4 per group) are the ratio of the intensities of the phosphorylated eIF2α to total eIF2α immunoblot bands, which is a measure of the extent of phosphorylation of this protein. As can be seen, the extent of phosphorylation of this protein in the apoE4 mice is higher than in the corresponding apoE3-expressing mice (*p<0.05, **p<0.01).

Figure 16:
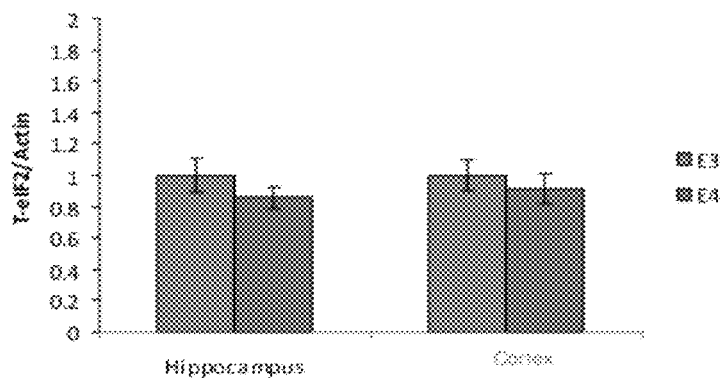

FIG. 16 demonstrates no modulation in the total amount of eIF2α protein (T-eIF2α) when compared with actin levels. This difference suggests that translation initiation is attenuated isoform-specifically in the apoE4 old mice both in the cortex and hippocampus.

Example 9

Figure 17:
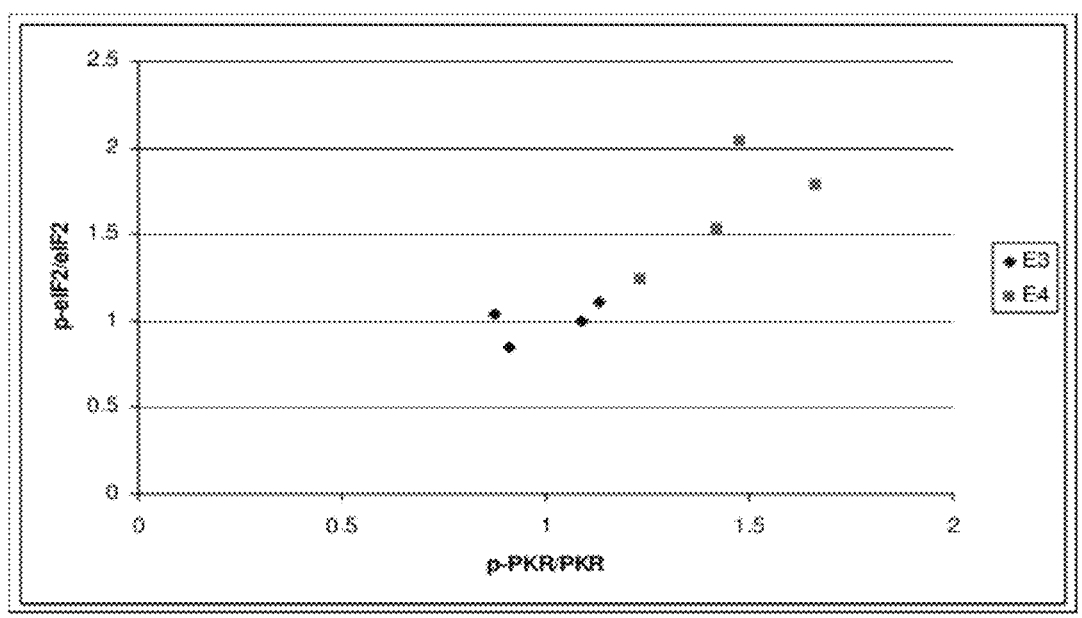
FIG. 17 shows the correlation between eIF2α and PKR phosphorylation in apoE4 transgenic mice.

Hippocampus of young (3-4 months) apoE3- or apoE4-expressing mice were homogenized and immunoblotted with antibodies that specifically recognise eIF2α or phosphorylated eIF2α (Ser 51), or PKR or pPKR (446). The results presented in FIG. 17 (n=4 per group) are the ratio of the intensities of the phosphorylated eIF2α to total eIF2α (y axis) or phosphorylated PKR to total PKR immunoblot bands, which is a measure of the extent of phosphorylation of these proteins. As can be seen, the extent of phosphorylation of these proteins in the apoE4 mice is higher than in the corresponding apoE3-expressing mice. Moreover, there is a clear correlation between eIF2α phosphorylation and PKR phosphorylation.

These results demonstrate surprisingly and unexpectedly that the main genetic risk factor for AD (i.e. expressing apoE4 and not apoE3) induces activation of the PKR-eIF2α axis in the brain. This activation impairs translation initiation and cognitive function. Thus, reversing the activation of this axis should not only enhance learning and memory as has been shown in the earlier Examples but also to target clear apoE4-dependent effect in the brain.

The above-described studies have enabled a better insight into the role of eIF-2α phosphorylation and its upstream regulators. To translate these findings into a new and powerful cognitive enhancer, the role of PKR, an upstream kinase of eIF-2α, was studied using both genetic and pharmacological (small molecule) approaches. Indeed, results demonstrate that levels of eIF-2α activity are critical for memory consolidation. Both PKR knockout animal models and specific small molecule inhibitors of PKR serve as cognitive enhancers in different learning paradigm subserved by different brain structures in the rodent brain. For example, i.p. injection of a PKR-specific inhibitor at the time of learning enhanced long term memory for fear conditioning (as determined by freezing assay). The enhanced memory was observed 24 hours and 2 weeks following acquisition, suggesting that this is indeed long term memory.

ApoE4 is the most prevalent genetic risk factor of AD, whereas the neurotoxic peptide amyloid-β (Aβ) is a key pathological hallmark of the disease. The cellular targets of these molecules and the mechanisms which mediate their effects are not known. Mediation of the pathological effects of apoE4 and Aβ were studied by impairing the ability of the neurons to handle insults and metabolic stress. Studies of AD brains have revealed a strong correlation between the level of phosphorylation of eIF2α and PKR, and neuronal degeneration. It was also found that the phosphorylated eIF2α co-localised with hyperphosphorylated tau. Increased activation of the eIF2α and mTOR pathways was also seen in lymphocytes of AD patients. Further experiments with transgenic mice that overexpress Aβ also revealed a correlation between phosphorylation of the eIF2α system and brain Aβ, suggesting that this phosphorylation is an early event.

The applicant has also shown the possibility that apoE4 interacts isoform-specifically with the eIF2α pathway. This revealed that whereas apoE4 and apoE3 mice had similar levels of eIF2α, this protein was hyperphosphorylated specifically in the apoE4 mice (See FIGS. 13 to 16). This proof of concept finding suggests that the translation mechanism is affected isoform-specifically by apoE4. This is the first indication that the main risk factor for AD (ApoE4) is inducing phosphorylation of eIF2α.

In light of the above-obtained results, the applicant has shown in addition that:
1. Malfunction of translation regulation and specifically the eIF-2α pathway may be correlated with early onset of AD.
2. Reducing the phosphorylation levels of eIF-2α in vivo using pharmacological or genetic approaches enhances cognitive function in animal models of AD.
3. Inhibition of eIF-2α phosphorylation can be used to treat dementia, or at least to improve cognitive function in patients with dementia thereby alleviating the most distressing symptoms of cognitive decline.
4. A major effect of the only gene (apoE4) known to be a risk factor in the most common form of AD (i.e. not familial) can be reversed.

The applicant has demonstrated that inhibition of eIF-2α phosphorylation results in improved cognitive function in vivo without any deleterious or toxic side-effects in a range of recognised tests. In particular, the applicant has demonstrated that this inhibition can be effected by inhibiting the kinase activity of PKR in a non-toxic manner by administering an inhibitor to animal models in vivo. The skilled person will appreciate that other inhibitors of eIF-2α phosphorylation could be used to achieve a similar effect. For example, the skilled person could readily design suitable peptide, antibody or nucleic acid inhibitors. These results offer a new platform and tools to delay the onset of cognitive dysfunction in AD and other forms of dementia.

Statistical Analysis

The results are expressed as means±SEM. For statistical analysis the paired t-test, t-test assuming equal variances, Levene's t-test for equality of variances, and the Univariate ANOVA test were used. For posthoc comparisons, Scheffe contrast test and LSD test were used with an α level of 0.05.

The invention claimed is:

1. A method for treating Alzheimer's disease, said method comprising administering to a patient in need of a therapeutically effective amount of the compound:

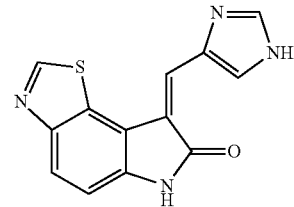

or a pharmaceutically acceptable salt thereof such as to treat Alzheimer's disease in said patient.

2. The method according to claim 1, wherein the compound is administered orally or by injection.

3. The method according to claim 1 wherein the compound inhibits eIF-2alpha kinase.

4. THE method according to claim 1 wherein the compound inhibits the kinase activity of PKR.

5. The method according to claim 1, wherein the patient is human.

* * * * *